United States Patent [19]

Puckette et al.

[11] Patent Number: 4,871,878

[45] Date of Patent: Oct. 3, 1989

[54] LOW PRESSURE RHODIUM CATALYZED HYDROFORMYLATION OF OLEFINS

[75] Inventors: Thomas A. Puckette; Thomas J. Devon, both of Longview, Tex.

[73] Assignee: Eastman Kodak Company, Rochester, N.Y.

[21] Appl. No.: 225,103

[22] Filed: Jul. 27, 1988

Related U.S. Application Data

[63] Continuation-in-part of Ser. No. 83,330, Aug. 10, 1987, abandoned.

[51] Int. Cl.$^4$ .............................................. C07C 45/50
[52] U.S. Cl. ................................................. 568/454
[58] Field of Search .......................................... 568/454

[56] References Cited

U.S. PATENT DOCUMENTS

| | | | |
|---|---|---|---|
| 4,420,640 | 12/1983 | Matsumoto et al. | 568/454 |
| 4,523,036 | 7/1985 | Cornils et al. | 568/454 |
| 4,528,403 | 7/1985 | Tano et al. | 568/454 |
| 4,533,755 | 8/1985 | Cornils et al. | 568/454 |
| 4,533,756 | 8/1985 | Lin et al. | 568/454 |
| 4,577,043 | 3/1986 | Kalbfell et al. | 568/454 |
| 4,578,523 | 3/1986 | Bahrmann et al. | 568/454 |
| 4,593,126 | 6/1986 | Cornils et al. | 568/454 |
| 4,593,141 | 6/1986 | Oswald et al. | 568/454 |
| 4,616,096 | 10/1986 | Cornils et al. | 568/454 |
| 4,740,626 | 4/1988 | Bahrmann et al. | 568/454 |
| 4,742,178 | 5/1988 | Nelson et al. | 568/454 |
| 4,755,624 | 7/1988 | Phillips et al. | 568/454 |
| 4,760,194 | 7/1988 | Philips et al. | 568/454 |

*Primary Examiner*—Werren B. Lone
*Attorney, Agent, or Firm*—S. E. Reiter; William P. Heath, Jr.

[57] ABSTRACT

The hydroformylation of olefins with rhodium complex catalysts is described. The catalysts employed comprise a rhodium complex with at least one phosphine having a specified structure, e.g., tris(benzyl)phosphine. Preferred phosphines have a pKa in the range of about 3.5 up to 5.3 and a cone angle in the range of about 160 up to 195°. Hydroformylation reactions at relatively low temperatures and pressure and yet with high rates of reaction and high selectivity to aldehyde product are obtained by the practice of the present invention.

19 Claims, No Drawings

LOW PRESSURE RHODIUM CATALYZED HYDROFORMYLATION OF OLEFINS

DESCRIPTION

This application is a continuation-in-part of Ser. No. 83,330, filed Aug. 10, 1987, hereby incorporated by reference in its entirety.

This invention relates to the rhodium catalyzed hydroformylation of olefins.

Background of the Invention

It is well known in the art to convert olefins to aldehydes having one additional carbon atom by contacting the olefin with hydrogen and carbon monoxide in the presence of a catalyst based on cobalt or rhodium metal. Rhodium-based catalysts have the advantage, relative to cobalt-based catalysts, of being able to promote the hydroformylation of olefins under less severe operating conditions.

One disadvantage of prior art rhodium-based catalysts is the propensity of such materials to lose activity over a period of time as a result, for example, of ligand decomposition. Triaryl phosphines, for example, are prone to conversion into alkyl diaryl phosphines under hydroformylation reaction conditions. These alkyl diaryl phosphines as rhodium ligands give lower activity catalysts compared to the triaryl phosphines.

Another disadvantage of prior art rhodium-based catalyst is the fact that not all rhodium salts are suitable starting materials for the preparation of rhodium complexes. For example, it is frequently observed that a several hour induction period is required to transform the rhodium complexes into active hydroformylation catalysts. This problem is particularly acute when halide containing compounds of rhodium are employed for the preparation of rhodium complexes.

Yet another disadvantage of rhodium-based catalyst systems is the high cost of the rhodium metal employed for catalyst preparation. Where one employs low levels of rhodium metal in order to reduce catalyst costs, low reaction rates frequently result.

There is, therefore, a continuing need in the field for high activity, high selectivity rhodium-based hydroformylation catalyst systems. Especially desirable would be high activity catalyst systems which can be controlled to produce a wide range of product ratios of normal/branched chain aldehyde products. Prior art rhodium-based hydroformylation catalyst systems typically lack such flexibility as they are only capable of producing very narrow normal/branched chain product ratios while at the same time retaining high catalyst activity. Efforts to vary the normal/branched chain product ratio significantly from that which a particular catalyst can inherently produce typically results in dramatically reduced catalyst activity.

Objects of the Invention

An object of the present invention, therefore, is a method for the rhodium-promoted hydroformylation of olefins to produce aldehydes in high yield and at a high rate of conversion.

Another object of the present invention is a method for the rhodium-promoted hydroformylation of olefins to produce aldehydes in a highly selective reaction, i.e., with very low levels of by-product formation.

Yet another object of the present invention is a rhodium complex catalyst which remains stable and soluble for extended periods of time under hydroformylation conditions.

Still another object of the present invention is a method for the rhodium-promoted hydroformylation of olefins employing low levels of rhodium and low levels of ligand for the rhodium catalyst.

A further object of the present invention is a method for the rhodium-promoted hydroformylation of olefins wherein the ratio of normal/branched chain aldehyde products can be varied within a wide range while retaining a high level of catalyst activity.

These and other objects of the present invention will become apparent from inspection of the detailed description and appended claims.

Statement of the Invention

In accordance with the present invention, we have discovered high selectivity, high activity rhodium catalysts for use in the hydroformylation of olefins. High yields of hydroformylation products are obtained with very low levels of undesired byproducts. These novel catalysts allow the hydroformylation of olefins to be carried out at low pressures with relatively low levels of rhodium catalyst and ligand therefor. In addition, the invention catalysts provide one with a great deal of control over the hydroformylation reaction due to the sensitivity of rhodium catalyst activity and selectivity (with respect to normal/branched chain ratios) to reaction conditions of temperature and $H_2/CO$ ratios, as well as the quantity of ligand employed.

DETAILED DESCRIPTION OF THE INVENTION

In accordance with the present invention, we have discovered a class of hydroformylation reaction catalysts which give high yield of hydroformylation product with high selectivity. Such reactions are promoted by soluble rhodium catalysts complexed with phosphine ligands having the following generic formula

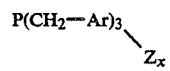

wherein Ar is an aromatic ring having 6–14 carbon atoms, e.g., phenyl, naphthyl, phenanthryl and anthracenyl;

each Z is independently:

a $C_1$ up to $C_{12}$ alkyl radical or substituted alkyl radical;

a $C_6$ up to $C_{12}$ aryl radical or substituted aryl radical;

a $C_7$ up to $C_{12}$ alkaryl or aralyl radicals or substituted alkaryl or aralkyl radicals;

a halogen (except Cl, Br or I in the ortho position);

—OR or —$CO_2R$, wherein R is Z;

—$SO_3M$, wherein M is H, an alkali metal or a quaternary ammonium moiety of the formula $NR_4^y$, wherein each $R^y$ is independently a $C_1$–$C_{20}$alkyl, aryl, aralkyl or alkaryl moiety;

and wherein x is a whole number which varies in the range of 0 up to 4 when Ar is phenyl, 0 up to 6 when Ar is naphthyl and 0 up to 8 when Ar is phenanthryl or anthracenyl.

Exemplary compounds which satisfy this generic formula include:

tribenzyl phosphine,
tris(3,4-dichlorobenzyl)phosphine,
tris(m-chlorobenzyl)phosphine, tris(p-chlorobenzyl)phosphine,
tris(o-fluorobenzyl)phosphine,
tris(m-fluorobenzyl)phosphine,
tris(p-methoxybenzyl)phosphine,
tris(m-methoxybenzyl)phosphine,
tris(m-methylbenzyl)phosphine,
tris(p-methylbenzyl)phosphine,
tris(3,5-dimethylbenzyl)phosphine,
tris([2,3]-benzobenzyl)phosphine,
tris(o-methylbenzyl)phosphine,
tris(p-tert-butylbenzyl)phosphine,
tris([3,4]-benzobenzyl)phosphine, and
tris(p-fluorobenzyl)phosphine.

Preferred phosphines are those which have a $C_3$ axis of symmetry, i.e., symmetrical triorgano-substituted phosphines. Such materials are preferred because they are readily prepared and readily purified. Purified phosphine is highly desirable because such materials facilitate the preparation of high activity rhodium-based catalysts.

The most preferred phosphines contemplated for use in the practice of the present invention are phosphines which have a pKa within the range of about 3.5 up to 5.3 and a cone angle within the range of about 160° up to 195°.

The pKa of phosphines is a measurement of the degree of reaction for the incomplete chemical reaction between the proton acceptor (phosphine) and a proton donor. The pKa is used as a measure of the relative basicities of the organophosphorus compounds. The term "pKa" is defined as the negative logarithm (to the base 10) of the equilibrium constant, Ka, for the proton acceptor-proton donor interaction referred to above. The stronger the base, the larger its pKa; for example, the pKa for the equilbrium between sulfuric acid, its conjugate base, the bisulfate ion, is about $-3.0$; the pKa for the equilibrium between acetic acid and its conjugate base, the acetate ion, is 4.76; and the pKa for the equilibrium between boric acid and its conjugate base, monobasic borate ion, is 9.24. Of the above examples, the monobasic borate ion, with the highest pKa value, is the strongest base.

The pKa values for numerous substituted phosphines have been measured and are reported by Streuli in *Anal. Chem.* 32, pp. 985–987 (1960). Those of skill in the art are aware of numerous methods by which pKa values can be determined, such as for example, non-aqueous titrimetry in nitromethane solvent, titration of solutions in mixed water methanol solvent systems, anhydrous acetic acid, acetic anhydride/toluene mixtures, acetic anhydride/dioxane mixtures, and the like.

The cone angle is a measure of the steric properties of the phosphine. In general terms, the cone angle is the smallest angle of a cone (with its apex at a specified point in the phosphine moiety) which would contain all of the hydrocarbyl groups attached to the phosphorus atom. A detailed discussion of the cone angle measurements and the significance thereof can be found in *Chem. Reviews*, 77, 313–348 (1977), in the article by Chadwick Tolman entitled "Steric Effects of Phosphorus Ligands in Organometallic Chemistry and Homogeneous Catalysis", to which article those of skill in the art are directed for more detail.

Many sources of rhodium can be used as the rhodium component for preparation of the catalyst of the invention, provided that the source of rhodium employed can be converted into soluble carbonyl-ligand complexes of rhodium. Suitable rhodium compounds include:

rhodium (I) dicarbonly acetonlyacetonates,
rhodium (II) 2-ethylhexanoate,
rhodium (II) acetate,
rhodium (0) carbonlys (e.g., $Rh_6(CO)_{16}$, $Rh_4(CO)_{12}$),
$HRh(CO)(Ph_3P)_3$, as well as mixtures of any two or more thereof.

It is preferred that non-halogen containing rhodium compounds be used to avoid problems of low catalyst activity caused by the presence of residual halide, to avoid the corrosive effects of residual halide ions, and the like. In addition, salts of strong mineral acids are undesirable sources of rhodium because these compounds release acids which are detrimental to rhodium catalyst activity under hydroformylation conditions.

We have found rhodium 2-ethylhexanoate to be a particularly preferred source of rhodium from which to prepare the complex catalyst of the invention because it is a convenient source of soluble rhodium, as it can be efficiently prepared from inorganic rhodium salts such as rhodium halides.

No special provisions are required for the preparation of the catalyst employed in the practice of the present invention, although it is preferred, for high catalyst activity, that all manipulations of the rhodium and phosphine components be carried out under an inert atmosphere, e.g., $N_2$, Ar, and the like. The desired quantities of a suitable rhodium compound and ligand are charged to the reactor in a suitable solvent. The sequence in which the various catalyst components are charged to the reactor is not critical. Thus, the rhodium component can be added to the reactor, then the phosphine component; or conversely, the phosphine component can be added to the reactor, then the rhodium component; or, alternatively, the preformed rhodium-phosphine complex can be charged to the reactor.

Suitable solvents, if one chooses to use solvent in the practice of the invention, include those which do not adversely affect the hydroformylation process and which are inert with respect to the catalyst, olefin, hydrogen and carbon monoxide feeds as well as the hydroformylation products. Inert solvents of this nature are well known to those of skill in the art and include such solvents as benzene, xylene, toluene, as well as their substituted derivatives; pentanes, naphtha, kerosene, mineral oils, cyclohexane, cyclopentane, ethers, esters, etheresters, alcohols, acetals, ketones, water, as well as various mixtures thereof. Preferred solvents are those which are sufficiently high boiling to remain, for the most part, in a gas sparged reaction, and include such compounds as 2,2,4-trimethyl-1,3-pentanediol monoisobutyrate (TMPDMI; available from the Eastman Chemicals Division of Eastman Kodak Company as Texanol® solvent), and its isomers, as well as the by-products of the hydroformylation reaction, such as alcohols, esters, acetals and hydroxyaldehydes which are retained as high boiling liquids at the bottom of subsequent distillation columns.

The catalyst produced by employing the above-described starting materials and procedure is believed to consist primarily of compounds of the structure:

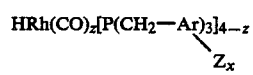

$$HRh(CO)_z[P(CH_2-Ar)_3]_{4-z}$$
$$Z_x$$

wherein Ar is an aromatic ring having 6–14 carbon atoms, e.g., phenyl, naphthyl, phenanthryl and anthracenyl;

each Z is independently:
a $C_1$ up to $C_{12}$ alkyl radical or substituted alkyl radical;
a $C_6$ up to $C_{12}$ aryl radical or substituted aryl radical;
a $C_7$ up to $C_{12}$ alkaryl or aralkyl radical or substituted alkaryl or aralkyl radical; halogen (except Cl, Br or I in the ortho position);
—OR or —$CO_2R$, wherein R is Z;
—$SO_3M$, wherein M is H, an alkali metal or a quaternary ammonium moiety of the formula $NR_4^y$, wherein each $R^y$ is independently a $C_1$–$C_{20}$ alkyl, aryl, aralkyl or alkaryl moiety;
wherein x is a whole number which varies in the range of 0 up to 4 when Ar is phenyl, 0 up to 6 when Ar is naphthyl and 0 up to 8 when Ar is phenanthryl or anthracenyl;
and wherein z is a whole number which varies in the range of 0 up to 3.

The process of the present invention can be carried out with widely varied amounts of rhodium. For example, amounts of catalyst containing as little as about $1 \times 10^{-6}$ moles of rhodium (calculated based on rhodium metal) per mole of olefin in the reactor zone can be employed. Such low catalyst concentrations are not generally commercially desirable since the reaction rates are frequently rather low. There is no upper limit as to operable catalyst concentrations, but such upper limit is generally determined by the high cost of rhodium metal and the fact that no advantage is generally obtained with catalyst amounts greater than about $1 \times 10^{-1}$ moles of rhodium per mole of olefin in the reactor zone. Concentrations in the range of about $1 \times 10^{-5}$ moles to about $5 \times 10^{-2}$ moles of rhodium per mole of olefin is preferred. Rhodium concentrations in the range of about $1 \times 10^{-4}$ up to $1 \times 10^3$ are most preferred because most efficient utilization of rhodium is obtained while the cost of the rhodium component is maintained within a commercially reasonable amount.

The molar ratios of phosphine to rhodium can vary over a wide range. Typically, the phosphine to rhodium ratio will vary within the range of about 2 up to 50. Preferably the molar ratio of phosphine to rhodium will vary within the range of 3 up to 30. In a most preferred embodiment, the molar ratio of phosphine to rhodium will vary within the range of about 6 up to 20. A particular advantage of the practice of the present invention is the fact that both catalyst activity and the ratio of normal to branched chain aldehyde products can be controlled by varying the phosphorus to rhodium ratio employed. For example, as higher ratios of phosphine to rhodium are employed, selectivity to the normal isomer (relative to the branched chain isomer) increases, while the reaction rate decreases.

Olefins contemplated for use in the practice of the present invention include straight chain, branched chain, or cyclic, terminal or internal mono-olefins containing in the range of 2 up to 20 carbon atoms and non-conjugated polyolefins typically having in the range of 5 up to 5,000 carbon atoms, e.g., polybutadiene, with each of the above optionally containing groups or substituents which do not interfere with the hydroformylation process. Such substituents which do not interfere with the hydroformylation process include:
—OH,
—OR''; wherein R'' is $C_1$ up to $C_{20}$ alkyl, aryl, alkaryl, aralkyl, or acyl radical,

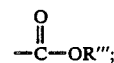

wherein R''' is a $C_1$ up to $C_{20}$ alkyl, aryl, alkaryl or aralkyl radical,

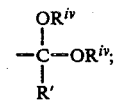

wherein R' is independently selected from H, $C_1$ up to $C_{12}$ alkyl radicals or substituted alkyl radicals, and $C_6$ up to $C_{12}$ aryl radicals or substituted aryl radicals, and each $R^{iv}$ is independently selected from the members defined by R', where the $R^{iv}$ groups can be joined together to form a cyclic acetal or ketal,
—SR''; wherein R'' is as defined above, and

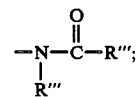

wherein R''' is as defined above.

Substituted derivatives of such olefins and non-conjugated polyolefins contemplated for use in practice of the present invention can be represented by the following formulae: alchols of the structure:

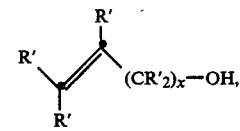

wherein each R' is independently selected from H, $C_1$ up to $C_{12}$ alkyl or alkylene radicals or substituted alkyl or alkylene radicals, and $C_6$ up to $C_{12}$ aryl radicals or substituted aryl radicals; and x is a whole number between 1 and 20;
compounds of the structure:

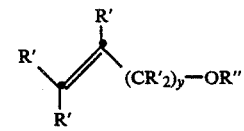

wherein R' is as defined above; R'' is $C_1$ up to $C_{20}$ alkyl, arly, alkaryl, aralkyl or acyl radical, and y is a whole number of 0 up to 20;
esters of the structure:

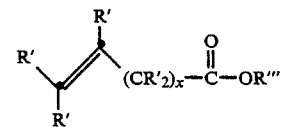

wherein R' and x are as defined above; and R''' is a $C_1$ up to $C_{20}$ alkyl, aryl, alkaryl or aralkyl radical;
acetals and ketals of the structure:

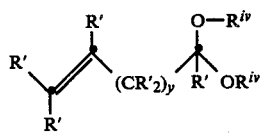

wherein R' and y are as defined above; and each $R^{iv}$ is defined as in R', plus, the two $R^{iv}$ groups may be joined together to form a cyclic acetal or ketal;

sulfides of the structure:

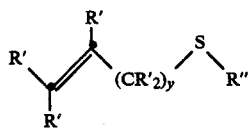

wherein R', R" and y are as previously defined; and amides of the structure:

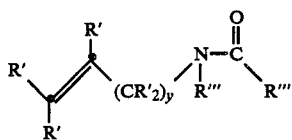

wherein R', R''', and y are as previously defined.

Exemplary alpha-olefins suitable for use in the practice of the present invention are ethylene, propylene, 1-butene, 2-methylpropylene, 2-methyl-1-butene, 1-pentene, 1-hexene, 1-heptene, 1-octene, 2-ethyl-1-hexene, 1-dodecene and 1-octadecene. Also useful in the practice of the present invention are the internal olefins such as 2-butene and cyclic olefins such as cyclooctene. If desired mixtures of olefins, particularly ethylene and propylene, can also be fed to the reactor.

Preferred olefins employed in the practice of the present invention contain in the range of 2 up to 10 carbon atoms, with olefins containing in the range of 2 up to 4 carbon atoms being preferred.

The process of the present invention can be carried out in any suitable reaction vessel. Suitable reaction vessels include gas sparged reactors, liquid overflow reactors, stirred tank reactors, trickle bed reactors, and the like, as are known to those of skill in the art.

A presently preferred reactor for carrying out the process of the present invention with low boiling products is a gas sparged reactor such that the catalyst does not leave the reaction zone with the aldehyde product which is taken overhead by unreacted gases. For higher boiling products, a liquid overflow type of reactor may be more appropriate to facilitate product handling and recovery.

With a gas sparged reactor, the overhead gases are chilled in a vapor liquid separator to condense out the aldehyde product, with the gases being recycled to the reactor while the liquid product is let down to atmospheric pressure for separation and purification by conventional means. A side draw from the reactor can optionally be provided for more complete product distillation. Small amounts of catalyst are withdrawn from the reactor along with the side draw of reaction medium. Following product recovery, the catalyst can optionally be subjected to appropriate regeneration treatment before being returned to the reactor, following the addition of make-up ligand thereto.

The process of the present invention is carried out at temperatures in the range of about 0° up to 190° C. Temperatures in the range of about 50° up to 150° C. are preferred, with temperatures in the range of 75° up to 125° C. being most preferred because reactions at such temperatures give excellent rate of reaction with minimum catalyst deactivation.

Pressures in the range of about 15 up to 1500 psia are typically employed for the hydroformylation reaction. Preferably, reaction pressure in the range of about 100 up to 450 psia are employed, with reaction pressures in the range of about 150 up to 250 psia being most preferred because economically attractive reaction rates are obtained at these relatively low reaction pressures, which in turn reduces the cost of reaction equipment, the need for added compressor capacity, gas recycle, etc.

Hydrogen to carbon monoxide ratios in the reaction zone can vary over a wide range. Typically, hydrogen to carbon monoxide ratios of about 0.5:1 up to 10:1 will be employed. Hydrogen to carbon monoxide ratios in the range of about 1:1 up to 6:1 are preferred, with ratios in the range of about 1.1:1 up to 5:1 being most preferred because high catalyst activity is obtained with minimum by-product formation when reaction is carried out at such ratios.

Contact times employed in the practice of the present invention can vary over a wide range. Reactant residence times in the range of seconds up to hours are operable. In terms of total gas flows, reactant space velocities typically fall in the range of 1 up to 1000 standard cubic feed per minute per cubic foot of catalyst (SCFM). Preferably, reactant space velocities in the range of 25 up to 200 SCFM are employed, with reactant space velocities in the range of 50 up to 125 SCFM being most preferred because at such space velocities, with relatively low molecular weight products such as butyraldehyde, a desirable balance is achieved between product production rate and fluid levels in the reaction vessel. At lower gas flow rates, the rate of reaction is limited by the level of reactant gas present in the reaction zone, while at higher gas flow rates, the reactor contents tend to be removed from the vessel faster than the rate of formation of additional product. The preferred gas flow rate with any given olefin feed will be a function of the total reactor pressure, reaction temperature, product production rate, and the like.

It is preferred that the reagents employed for the invention hydroformylation process be substantially free of materials which may reduce catalyst activity or completely deactivate the catalyst. Thus, such materials as conjugated dienes, acetylenes, mercaptans, mineral acids, halogenated organic compounds, and free oxygen should generally be excluded from the reaction. It is of note that no special precautions regarding the exclusion of water need be taken, as small amounts of water have not been found to be detrimental to the invention hydroformylation process.

The invention will now be illustrated further by reference to the following non-limiting examples.

EXAMPLES

The reactor employed for the hydroformylation reaction described in the Examples consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain precise flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen is passed through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a tank containing liquid propylene using an armored rotameter with a needle valve to control the liquid propylene feed rate.

In operation, the catalyst is contained as a solution in the lower portion of the reactor tube and the reactant gases are sparged up through the solution as bubbles emanating from the filter element. Product butyraldehyde is formed in the catalyst solution where it accumulates and eventually is removed as a vapor by vapor/liquid equilibration with unreacted gases. This type of reactor is known as a vapor take-off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected.

In practice, approximately one hour is required for this reaction unit to achieve a regime where catalyst activity and n/iso product ratios to reach substantially constant levels.

EXAMPLE 1

Demonstration of Catalyst Stability

A catalyst charge comprised of 0.044 gram of rhodium (as rhodium 2-ethylhexanoate) and 1.35 grams of tribenzylphosphine dissolved in 0.175 liter 2,2,4-trimethyl-1,3-pentaneodiol monoisobutyrate was charged to the reactor system described above. The reactor was maintained under the following conditions:
Experimental Conditions:
$H_2/CO$ ratio - 1:1
$H_2$ flow rate - 2.5 liters/min.
CO flow rate - 2.5 liters/min.
Propylene gas flow - 1.92 liters/min. (at STP).
Total reaction pressure - 200 psig.
Reaction temperature - 120° C.

The reactor was operated continuously for 9 days under the conditions set forth above. After a line-out period of 48 hours during which the catalyst activity slowly and steadily increased, the catalyst produced aldehydes with a normal to branched isomer ratio of 1.65 to 1.69 at a production rate of 5.62 to 5.90 pounds of butyraldehyde per gram of rhodium per hour (lb. HBu/g-Rh-hr.). There was no detectable change in production rate or isomer distribution after the 48-hr. line-out period.

At the end of the ninth day, an additional 2.90 grams of tribenzylphosphine was added to the catalyst. The normal to branched isomer ratio increased to 1.85 while the production rate declined to 3.23 to 3.51 (lb. HBu/g-Rh-hr.). The reaction was continued for an additional 3 days during which no further changes in isomer distribution or production rate were observed. The recovered catalyst was light yellow liquid, free of any solids.

EXAMPLE 2

Effect of Varying Carbon Monoxide Partial Pressure

A catalyst charge comprised of 12 mg of rhodium (as rhodium 2-ethylhexanoate) and 1.24 grams of tribenzylphosphine dissolved in 0.175 liter of Texanol® was charged to the reactor system described above. The reactor was maintained at 110° C. and operated continuously for seven hours. The reaction was conducted in the same manner as set forth in Example 1, except that the $H_2/CO$ ratio was changed as noted in Table 1.

TABLE 1

Effects of Varying $H_2/CO$ Ratio in Synthesis Gas Feed - (Example 2)

| Hour | $H_2/CO$ Mole Ratio | Total Synthesis Gas Feed, 1/min at STP | $C_3H_6$ Feed, moles/hr | N/I Ratio |
|---|---|---|---|---|
| 1 | 1.0 | 5.0 | 5.15 | 1.76 |
| 2 | 1.0 | 5.0 | 5.15 | 1.88 |
| 3 | 1.0 | 5.0 | 5.15 | 1.91 |
| 4 | 1.0 | 5.0 | 5.15 | 1.91 |
| 5 | 1.5 | 5.0 | 5.15 | 1.94 |
| 6 | 1.5 | 5.0 | 5.15 | 1.94 |
| 7 | 2.0 | 5.0 | 5.15 | 2.01 |

The results set fourth above demonstrate that the normal/iso (or branched) ratio for product aldehyde is increased by greater than 10% by merely increasing the $H_2/CO$ ratio.

EXAMPLE 3

Effect of Temperature on n/iso Product Ratios

A catalyst charge comprised of 31.25 mg of rhodium (as rhodium 2-ethylhexanoate) and 1.69 grams of tribenxylphosphine dissolved in 0.2 liter of Texanol® solvent was charged to the reactor system described above. The reactor was maintained at a temperature in the range of about 100 up to 135° C., as noted in Table 2, and operated continuously for seven hours. The reaction was conducted according to the general procedure set forth above. Operating parameters and reaction results are set forth in Table 2.

TABLE 2
Effect of Temperature on n/iso Ratio with Rhodium-Tribenzylphosphine Catalyst

| Average Reactor Temperature, °C. | N/I | Intrinsic Activity, lbs HBu/gRh-hour | Free Ligand Conc. mmole/liter |
| --- | --- | --- | --- |
| 100.1 | 1.83 | 3.20 | 19.58 |
| 110.0 | 1.74 | 4.88 | 20.72 |
| 115.0 | 1.68 | 6.42 | 20.15 |
| 119.0 | 1.60 | 7.41 | 19.70 |
| 125.6 | 1.54 | 8.30 | 20.52 |
| 129.8 | 1.46 | 8.41 | 20.92 |
| 134.7 | 1.38 | 8.90 | 20.18 |

| Experimental Conditions | | Partial Pressures in Feed | |
| --- | --- | --- | --- |
| Rhodium Conc. | 140 ppm | Hydrogen | 96 psia |
| Total Pressure | 260 psig | Carbon Monoxide | 96 psia |
| | | Propylene | 55 psia |
| | | Nitrogen | 27.5 psia |
| Total reactor feed - 9.6 liters/min. @ STP | | | |

The above data demonstrate that varying reaction temperature is an effective way to control the normal-/iso product ratio. An increase in the normal/iso ratio of greater than 30% is observed with a variation in reaction temperature of less than 35° C.

EXAMPLE 4

Effect of Ligand Concentration on n/iso Ratio with Rhodium-Tribenzylphosphine Catalyst A catalyst charge comprised of 31.25 mg of rhodium (as rhodium 2-ethylhexanoate) and varying amounts of tribenzylphosphine (as noted in Table 3) dissolved in 0.2 liter of Texanol ® solvent was charged to the reactor system described above. The reactor was maintained at 125° C. and operated continuously for seven hours. The reaction was conducted according to the general procedure set forth above. Operating parameters and reaction results are set forth in Table 3.

TABLE 3
Effect of Ligand Concentration on n/iso Ratios with Rhodium-Tribenzylphosphine Catalysts

| Free Ligand Conc. mmol per liter | N/I Ratio | Intrinsic Activity lbs HBu/gRh-h |
| --- | --- | --- |
| 6.57 | 1.35 | 10.80 |
| 16.50 | 1.46 | 6.84 |
| 19.40 | 1.47 | 7.91 |
| 20.50 | 1.48 | 7.57 |
| 36.10 | 1.55 | 6.00 |
| 55.60 | 1.65 | 4.53 |

| Experimental Conditions | | Reactor Feed Composition | |
| --- | --- | --- | --- |
| Total Pressure | 260 psig | Hydrogen | 96 psia |
| Rhodium Conc. | 140 ppm | Carbon Monoxide | 96 psia |
| Reactor Temp. | 125° C. | Propylene | 55 psia |
| | | Nitrogen | 27.5 psia |
| Total Reactor Flow 9.6 liter/minute | | | |

These results demonstrate that higher normal/iso ratios (20% increase demonstrated) are obtained when higher ligand concentrations are employed.

EXAMPLE 5

Hydroformylation of Propylene with Tribensylphosphine and Substituted Tribensylphosphine-Rhodium Catalysts A catalyst charge comprised of 15 mg of rhodium (as rhodium 2-ethylhexanoate) and varying amounts of tribenzylphosphine or tirbenzylphosphine derivative (as noted in Table 4) dissolved in 0.2 liter of Texanol ® solvent was charged to the reactor system described above. The reactor was maintained at 125° C. and operated continuously for seven hours. The reaction was conducted according to the general procedure set forth above. Operating parameters and reaction results are set forth in Table 4.

TABLE 4
Hydroformylation of Propylene with Rhodium Tribenzylphosphine and Derivatives Thereof

| Run No. | Substituent on Aromatic Ring | n/iso Ratio | Intrinsic Activity lbs Hbu/g-Rh-hr | Ligand Conc. mmol/liter |
| --- | --- | --- | --- | --- |
| 1 | p-fluoro | 1.42 | 11.98 | 20.11 |
| 2 | p-fluoro | 1.35 | 14.05 | 8.72 |
| 3 | m-fluoro | 1.35 | 14.11 | 19.72 |
| 4 | 3,4-dichloro | 1.33 | 4.93 | 20.65 |
| 5 | 3,4-dichloro | 1.19 | 12.02 | 8.09 |
| 6 | 3,5-dimethyl | 1.55 | 12.69 | 10.58 |
| 7 | 3,5-dimethyl | 1.60 | 9.20 | 14.08 |
| 8 | m-fluoro | 1.30 | .17.72 | 8.25 |
| 9 | p-methoxy | 1.62 | 11.61 | 6.82 |
| 10 | p-methoxy | 1.44 | 19.00 | 1.57 |
| 11 | p-t-butyl | 1.68 | 12.13 | 18.19 |
| 12 | p-t-butyl | 1.48 | 20.14 | 6.28 |
| 13 | p-chloro | 1.52 | 6.34 | 21.16 |
| 14 | p-chloro | 1.27 | 21.65 | 5.16 |
| 15 | p-methyl | 1.63 | 10.42 | 19.76 |
| 16 | p-methyl | 1.46 | 18.23 | 6.85 |
| 17 | none | 1.37 | 19.26 | 4.89 |
| 18 | none | 1.48 | 14.81 | 9.23 |
| 19 | none | 1.50 | 12.32 | 17.68 |
| 20 | none | 1.67 | 8.73 | 39.17 |
| 21 | m-methoxy | 1.54 | 13.56 | 19.24 |
| 22 | 3,4-benzo (naphthyl) | 1.40 | 16.43 | 2.87 |
| 23 | 2,3-benzo (naphthyl) | 1.33 | 12.00 | 14.00 |
| 24 | o-methyl | 1.26 | 15.00 | 20.21 |

| Operating Conditions | | Partial Pressures in Feed | |
| --- | --- | --- | --- |
| Rhodium | 70 ppm | Hydrogen | 95 psia |
| Total Pressure | 260 psig | Carbon monoxide | 95 psia |
| Reactor Temperature | 125° C. | Propylene | 58 psia |
| | | Nitrogen | 27 psia |
| Total reactor feed - 9.6 liters/min. @ STP | | | |

These data demonstrate the operability of numerous substituted tribenzyl phosphines for the hydroformylation of olefins. Note the wide range of normal/iso ratio products which can be obtained under comparable reaction conditions. Thus, by choice of the appropriate substituted tribenzyl-phosphine, a great deal of control can be exercised over the ultimate hydroformylation product mix.

The invention has been described in detail with reference to particular embodiments thereof. It will be understood, however, that variations and modifications can be effected within the spirit and scope of the invention.

I claim:

1. A method for the hydroformylation of unsaturated compounds to product aldehydes, wherein said unsaturated compounds are selected from the group consisting of:
   $C_2$ up to $C_{20}$ mono-olefins,
   non-conjugated polyolefins, and
   substituted derivatives thereof, wherein the substituted derivatives contain one or more of the substituents selected from the group consisting of:
   —OH,
   —OR''; wherein R'' is $C_1$ up to $C_{20}$ alkyl, aryl, alkaryl, aralkyl, or acyl radical,

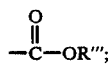

wherein R''' is a $C_1$ up to $C_{20}$ alkyl, aryl, alkaryl or aralkyl radical,

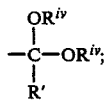

wherein R' is independently selected from H, $C_1$ up to $C_{12}$ alkyl radicals or substituted alkyl radicals, and $C_6$ up to $C_{12}$ aryl radical or substituted aryl radicals, and each $R^{iv}$ is independently selected from the members defined by R', where the $R^{iv}$ groups can be joined together to form a cyclic acetal or ketal, —SR''; wherein R'' is as defined above, and

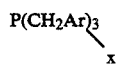

wherein R''' is as defined above,
said method comprising contacting at least one of said olefins with a soluble rhodium catalyst complexed with at least one phosphine compound having the following generic formula

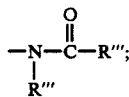

wherein Ar is an aromatic ring having 6–14 carbon atoms;

each Z is independently:
- a $C_1$ up to $C_{12}$ alkyl radical or substituted alkyl radical;
- a $C_6$ up to $C_{12}$ aryl radical or substituted aryl radical;
- a $C_7$ up to $C_{12}$ alkaryl or aralkyl radicals or substituted alkaryl or aralkyl radicals;
- a halogen (except Cl, Br or I in the ortho position);
- —OR or —$CO_2R$, wherein R is Z;
- —$SO_3M$, wherein M is H, an alkali metal or a quaternary ammonium moiety of the formula $NR_4^v$, wherein each $R^v$ is independently a $C_1$–$C_{20}$ alkyl, aryl, aralkyl or alkaryl moiety;

and wherein x is a whole number which varies in the range of 0 up to 4 when Ar is phenyl, 0 up to 6 when Ar is naphthyl and 0 up to 8 when Ar is phenanthryl or anthracenyl, in the presence of hydrogen and carbon monoxide at a temperature in the range of 0 up to 190° C., an absolute pressure of hydrogen plus carbon monoxide within the range of about 15 up to 1500 psia, and a reactant space velocity in terms of volumes of reactant gas per volume of catalyst in the range of 1 up to 1000 standard cubic feet per minute.

2. A method in accordance with claim 1 wherein Ar is selected from the group consisting of: phenyl, naphthyl, phenanthryl and anthracenyl.

3. A method in accordance with claim 1 wherein the ratio of hydrogen to carbon monoxide falls within the range of 0.5:1 up to 5:1.

4. A method in accordance with claim 1 wherein the substituted derivatives of said olefins and nonconjugated polyolefins are selected from the group consisting of alcohols of the structure

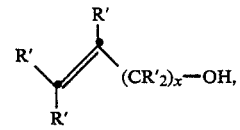

wherein each R' is independently selected from H, $C_1$ up to $C_{12}$ alkyl or alkenyl radicals or substituted alkyl or alkenyl radicals, and $C_6$ up to $C_{12}$ aryl radicals or substituted aryl radicals; and x is a whole number between 1 and 20;

compounds of the structure;

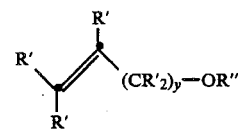

wherein R' is as defined above; R'' is $C_1$ up to $C_{20}$ alkyl, aryl, alkaryl, aralkyl or acyl radical, and y is a whole number of 0 up to 20;

esters of the structure

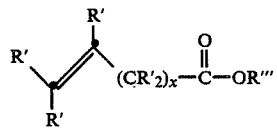

wherein R' and x are as defined above; R''' is a $C_1$ up to $C_{20}$ alkyl, aryl, alkaryl or aralkyl radical;

acetals and ketals of the structure:

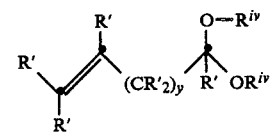

wherein R' and y are as defined above; and each $R^{iv}$ is defined as in R', plus, the two $R^{iv}$ groups may be joined together to form a cyclic acetal or ketal;

sulfides of the structure

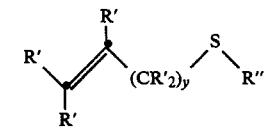

wherein R', R'' and y are as previously defined; and amides of the structure:

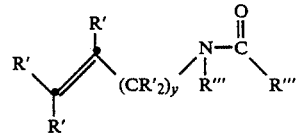

wherein R', R''', and y are as previously defined.

5. A method in accordance with claim 1 wherein said phosphine is selected from the group consisting of:
tribenzyl phosphine,
tris(3,4-dichlorobenzyl)phosphine,
tris(m-chlorobenzyl)phosphine,
tris(p-chlorobenzyl)phosphine,
tris(o-fluorobenzyl)phosphine,
tris(m-fluorobenzyl)phosphine,
tris(p-methoxybenzyl)phosphine,
tris(m-methoxybenzyl)phosphine,
tris(m-methylbenzyl)phosphine,
tris(p-methylbenzyl)phosphine,
tris(3,5-dimethylbenzyl)phosphine,
tris([2,3]-benzobenzyl)phosphine,
tris(o-methylbenzyl)phosphine,
tris(p-tert-butylbenzyl)phosphine,
tris([3,4]-benzobenzyl)phosphine, and
tris(p-fluorobenzyl)phosphine.

6. A method in accordance with claim 1 wherein said olefin or non-conjugated polyolefin is a $C_2$ up to $C_{10}$ hydrocarbon or substituted derivative thereof.

7. A method in accordance with claim 1 wherein the contacting of said olefin with said catalyst is carried out at a temperature in the range of 50° up to 150° C. and an absolute pressure of hydrogen plus carbon monoxide in the range of 100 up to 450 psia.

8. A method in accordance with claim 7 wherein the ratio of hydrogen to carbon monoxide falls within the range of 1:1 up to 3:1.

9. A method in accordance with claim 8 wherein the reactant space velocity falls within the range of 25 up to 200 standard cubic feet per minute per cubic foot of catalyst solution.

10. A method in accordance with claim 1 wherein said contacting is carried out at a temperature in the range of 75° up to 125° C. and an absolute pressure of hydrogen plus carbon monoxide in the range of 150 up to 250 psia.

11. A method in accordance with claim 10 wherein the ratio of hydrogen to carbon monoxide falls within the range of 1.1:1 up to 2.5:1.

12. A method in accordance with claim 11 wherein the reactant space velocity falls within the range of 50 up to 125 standard cubic feet per minute per cubic foot of catalyst solution.

13. A method in accordance with claim 1 wherein the quantity of rhodium employed for said hydroformylation varies within the range of 10 up to 50,000 parts per million.

14. A method in accordance with claim 13 wherein the molar ratio of phosphine to rhodium varies within the range of 2 up to 50.

15. A method in accordance with claim 1 wherein the quantity of rhodium employed for said hydroformylation varies within the range of 50 up to 1000 ppm.

16. A method in accordance with claim 15 wherein the molar ratio of phosphine to rhodium varies within the range of 3 up to 30.

17. A method in accordance with claim 1 wherein the quantity of rhodium employed for said hydroformylation varies within the range of 90 up to 250 parts per million.

18. A method in accordance with claim 17 wherein the molar ration of phopshine to rhodium varies within the range of 6 up to 20.

19. A method in accordance with claim 1 wherein the contacting of said olefin with said catalyst is carried out in the presence of a solvent selected from the group consisting of:
benzene,
toluene,
xylene,
pentanes,
naphtha,
cyclopentane,
ethers,
esters,
etheresters,
alcohols,
acetals,
ketals,
water,
and mixtures of any two or more thereof.

* * * * *

UNITED STATES PATENT AND TRADEMARK OFFICE
CERTIFICATE OF CORRECTION

PATENT NO. : 4,871,878

DATED : 10-03-89

INVENTOR(S) : Thomas A. Puckette and Thomas J. Devon

It is certified that error appears in the above-identified patent and that said Letters Patent is hereby corrected as shown below:

Claim 1, Column 12, line 58, "product" should be "produce".

Claim 1, Column 13, lines 22-25,

" 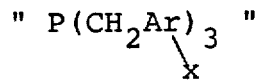 "

should be

"  "

Claim 1, Column 13, lines 33-35,

" 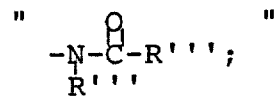 "

should be

" 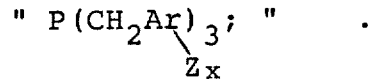 "

Claim 4, Column 14, line 14, there should be a "space" after $C_{12}$.

UNITED STATES PATENT AND TRADEMARK OFFICE
CERTIFICATE OF CORRECTION

PATENT NO. : 4,871,878
DATED : October 3, 1989
INVENTOR(S) : Thomas A. Puckette et al It is certified that error appears in the above-identified patent and that said Letters Patent is hereby corrected as shown below:

Claim 4, Column 14, line 15, there should be a "space" after $C_6$.

Signed and Sealed this

Twenty-third Day of October, 1990

Attest:

HARRY F. MANBECK, JR.

*Attesting Officer*          *Commissioner of Patents and Trademarks*